United States Patent [19]
Yanagita et al.

[11] Patent Number: 5,982,953
[45] Date of Patent: *Nov. 9, 1999

[54] IMAGE DISPLAYING APPARATUS OF A PROCESSED IMAGE FROM TEMPORALLY SEQUENTIAL IMAGES

[75] Inventors: Akiko Yanagita; Hitoshi Yoshimura; Hisashi Yonekawa; Fumio Shimada; Atsushi Kido, all of Tokyo, Japan

[73] Assignee: Konica Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/517,534

[22] Filed: Aug. 21, 1995

[30] Foreign Application Priority Data

Sep. 2, 1994 [JP] Japan .................................. 6-209768
Sep. 2, 1994 [JP] Japan .................................. 6-209769

[51] Int. Cl.$^6$ .............................. G06K 9/00; G06K 9/32; H04N 1/40; A62B 1/04
[52] U.S. Cl. .......................... 382/294; 382/128; 358/448; 348/65; 348/580; 364/731
[58] Field of Search ..................... 382/128, 168, 382/294; 358/404, 448; 348/65, 580; 364/731

[56] References Cited

U.S. PATENT DOCUMENTS

| | | | |
|---|---|---|---|
| 5,086,392 | 2/1992 | Nakajima | 382/128 |
| 5,101,827 | 4/1992 | Goldenberg | 424/1.49 |
| 5,196,928 | 3/1993 | Karasawa et al. | 348/65 |
| 5,340,988 | 8/1994 | Kingsley et al. | 250/370.09 |
| 5,357,580 | 10/1994 | Forestieri et al. | 382/128 |
| 5,359,513 | 10/1994 | Kano et al. | 382/128 |
| 5,467,202 | 11/1995 | Washio et al. | 358/448 |
| 5,523,786 | 6/1996 | Paruiski | 348/269 |

FOREIGN PATENT DOCUMENTS 61-14553 4/1986 Japan .
63-278183 11/1988 Japan .

*Primary Examiner*—Phuoc Tran
*Assistant Examiner*—Daniel G. Mariam
*Attorney, Agent, or Firm*—Frishauf, Holtz, Goodman, Langer & Chick, P.C.

[57] ABSTRACT

An image displaying apparatus includes a memory, an image reader, an image processor, an image adder and a display. The memory stores a plurality of medical images including temporally sequential images of a common portion of a same patient taken at different points of time. The image reader reads out the plurality of medical images from the memory. The image processor processes at least two of the plurality of medical images read out from the memory according to registration information of the at least two of the plurality of medical images so as to obtain a processed image. The image adder adds one of the plurality of medical images read out from the memory to the processed image so as to obtain an addition image. And the display displays the addition image.

8 Claims, 17 Drawing Sheets

Pixel value of a processed image from temporally sequential images

Pixel value of a processed image from temporally sequential images

Processed image from temporally sequential images

Processed image from temporally sequential images

Processed image from temporally sequential images in which the processing condition has been changed

IMAGE DISPLAYING APPARATUS OF A PROCESSED IMAGE FROM TEMPORALLY SEQUENTIAL IMAGES

BACKGROUND OF THE INVENTION

The present invention relates to an image displaying apparatus of a processed image from temporally sequential images. More particularly, the present invention relates to a technique by which a change in a radiographic object caused with the lapse of time is clearly shown in accordance with a processed image from temporally sequential images obtained when a plurality of temporally sequential images are subjected to image processing.

Radiographic images such as X ray images are frequently used for the diagnosis of a disease. In order to obtain X ray images, film-screen systems are conventionally used. In a film-screen system, X rays that have been transmitted through a radiographic object are irradiated on a phosphor layer (phosphor screen) so that visible luminescence is generated from the phosphor layer. The thus generated visible luminescene is irradiated on a silver halide film.

Using radiographs obtained in the above manner, medical diagnosis is conducted by a doctor as follows. For example, a plurality of radiographs are taken of the same patient at different points of time. After a plurality of radiographs have been obtained, for example, after chest radiographs of a patient to be examined have been taken in a routine medical checkup, the radiographs are observed by a doctor using a viewing box. In the process of observation, the doctor checks the temporally sequential images, and in accordance with his experience, he recognizes a change caused with the lapse of time, which is called an interval change. The result of observation is used for the medial diagnosis.

The above method in which temporally sequential images are compared with each other is called comparison reading. The method is important to find a change newly caused by a disease and also to recognize a progress or improvement of a disease.

However, even when the temporally sequential images are compared with each other in the above manner, an important interval change caused by a disease may be overlooked in some cases.

For example, bones, blood vessels, bronchus and other anatomic structures are sometimes combined with each other in a complicated manner on a radiographic image of the chest. Therefore, it is sometimes difficult to find a change on the image caused by a disease, because the change is camouflaged by the normal anatomic structures of bones, blood vessels, bronchus and other anatomy. Further, the density and contrast of two radiographs are usually different from each other due to the difference of an amount of exposure of X rays irradiated in the process of radiographing. Because of the fluctuation of density and contrast on the temporally sequential images on two radiographs, it is difficult to compare the two temporally sequential images with accuracy.

In comparison readings, it is necessary to select the films stored in a storage and bring them back to the reading room. Further, it is necessary to set the films on the viewing box prior to observation. This is inefficient in terms of time and labor.

According to the conventional method, moreover, even if a portion in which an interval change caused by a disease is found, it is necessary for the doctor to use his experience and knowledge for recognizing and judging the accurate position, range and degree of the change on the image caused by a disease. Therefore, the conventional technique makes it difficult to enhance the efficiency of medical diagnosis.

SUMMARY OF THE INVENTION

The present invention has been accomplished to solve the above problems. It is an object of the present invention to enhance the accuracy and efficiency of medical diagnosis when a doctor inspects radiographic images for medical use. According the present invention, a change in a portion on the radiographic image is clearly shown to a doctor using temporally sequential images, and further a positional relation between the changed portion on the radiographic image and the normal structures, which is not temporally changed, are clearly shown to the doctor.

In order to accomplish the above object, an image displaying apparatus of a first embodiment of the present invention comprises: a storage unit for storing a plurality of images; an image reading means for reading out a plurality of images including the common portion of a subject from the storage section; an image processing section for processing at least two images read out by the image reading means so as to obtain a processed image from temporally sequential images; an image addition means for adding an original image read out by the image reading means to the processed image generated by the image processing means; and an image displaying means for displaying the addition image generated by the image addition means.

An image displaying apparatus of a second embodiment of the present invention comprises: a storage unit for storing a plurality of images; an image reading means for reading out at least one image processed from temporally sequential images including the common portion of a subject and also reading out at least one original image that has not been processed from temporally sequential images, wherein these images are read out from the storage unit; an image addition means for adding the original image to the processed image from temporally sequential images that has been read out by the image reading means; and an image displaying means for displaying the addition image generated by the image addition means.

An image displaying apparatus of a third embodiment of the present invention comprises: a storage unit for storing a plurality of images; an image reading means for reading out a plurality of images including the common portion of a subject from the storage section; an image processing means for processing at least two images read out by the image reading means so as to obtain a processed image from temporally sequential images; an image displaying means for displaying the processed image by the image processing means; and a control means for simultaneously displaying the image read out by the image reading means and the processed image from temporally sequential images by the image processing means, the image displaying apparatus further comprises a plurality of screens, the resolutions of which are different from each other, and at least one of the displayed images is displayed on a screen, the resolution of which is relatively high, and the processed image from temporally sequential images is displayed on a screen, the resolution of which is relatively low.

An image displaying apparatus of a fourth embodiment of the present invention comprises: a storage unit for storing a plurality of images; an image reading means for reading out a plurality of images including the common portion of a subject from the storage section; an image processing means for processing at least two images read out by the image reading means so as to obtain a processed image from temporally sequential images; an image displaying means for displaying the processed image by the image processing means; and a control means for simultaneously displaying the image read out by the image reading means and the processed image from temporally sequential images by the image processing means, wherein the reduction ratios of other images are relatively higher than the reduction ratio of at least one original image displayed by the image displaying means.

An image displaying apparatus of a fifth embodiment of the present invention comprises: a storage unit for storing a plurality of images; an image reading means for reading out a plurality of images including the common portion of a subject from the storage section; an image processing means for processing at least two images read out by the image reading means so as to obtain a processed image from temporally sequential images; an image displaying means for displaying the processed image by the image processing means; a control means for simultaneously displaying the image read out by the image reading means and the processed image from temporally sequential images by the image processing means; a reference region setting means for setting a reference region on one reference image in the plurality of images; and a comparative image setting means for setting a comparative region corresponding to the above reference region on at least one comparative image except for the reference image in the plurality of images.

An image displaying apparatus of a sixth embodiment of the present invention comprises: a storage unit for storing a plurality of images; an image reading means for reading out a plurality of images including the common portion of a subject from the storage section; an image processing means for processing at least two images read out by the image reading means so as to obtain a processed image from temporally sequential images; an image displaying means for displaying the processed image by the image processing means; a control means for displaying the image read out by the image reading means and the processed image from temporally sequential images by the image processing means, wherein these images are alternately displayed on the image displaying means, and the image processing means conducts a processing for compensating a difference between the image read out by the image reading means and the reference image, on the images except for the reference image.

According to the displaying apparatus of a processed image from temporally sequential images of the first embodiment of the present invention, the original image stored in the storage unit and the image processed from temporally sequential images corresponding to the original image are added, and the addition image is displayed.

Processing from temporally sequential images is a subtraction processing conducted between the images processed from temporally sequential images. By this subtraction processing, normal anatomic structures, which are unchanged, are canceled, and a portion, which has been temporally changed, is selectively emphasized. Further, when the subtraction image is added to the original image, which is the image processed from temporally sequential images used for making the subtraction image, a positional relation between the portion which has been temporally changed and the portion which has not been temporally changed can be clearly shown.

However, when the image processed from temporally sequential images and the original image are added as they are, the portion with an interval change, which has been emphasized by the image processed from temporally sequential images, tends to be camouflaged by the normal complicated structures on the original image. Therefore, according to the present invention, after at least one of the original image and the processed image from temporally sequential images has been subjected to image processing, the addition processing is conducted. In this way, the portion with an interval change or the portion without an interval change can be clearly distinguished on the addition image.

According to the displaying apparatus of a processed image from temporally sequential images of the second embodiment of the present invention, the storage unit stores a plurality of temporally sequential original images, and there is provided a means for generating an image processed from temporally sequential images using the original images. In the same manner as the first embodiment, image processing is conducted, and the original images and the processed image from temporally sequential images are added, so that the addition image is displayed on the displaying apparatus.

According to the image displaying apparatus of the third embodiment, a plurality of images including the common portion of a subject, which have previously been stored in the storage unit, are read out, and at least two images which have been read out in this way are simultaneously displayed on the screen. In the manner described above, the plurality of images including the common portion of a subject can be relatively easily compared with each other. Therefore, it is possible to simplify the complicated work otherwise necessary for image reading. When a plurality of screens, the resolution of which is different from each other, are provided, the operation is conducted as follows. For example, an original image (the newest image in the temporal sequential images) used for the reference of medical diagnosis is displayed on the screen, the resolution of which is high, and a processed image from temporal sequential images used for the comparison of the diagnosis is displayed on the screen, the resolution of which is low. In this way, the performance of medical diagnosis can be enhanced in the process of reading the original images, and the cost required for maintaining the resolution of the displaying means can be reduced to the minimum.

In the image displaying apparatus of the fourth embodiment of the present invention, the size of at least one image displayed on the screen is reduced. Therefore, when a plurality of images are simultaneously displayed on the same screen, it is easy to compare the images with each other in the process of reading the images. In the plurality of images that are simultaneously displayed, the image reduction ratios are made to be different from each other. For example, the size of a reference image is relatively large when it is displayed, so that the image can be read easily. On the other hand, the size of a comparison image (for example, the image processed from temporally sequential images, or the image processed from temporally sequential images in the past) is relatively small when it is displayed, so that the screen can be effectively utilized.

In the image displaying apparatus of the fifth embodiment of the present invention, a plurality of images having the common radiographic object portion are read out and displayed on the same screen or the different screens. In this case, when a reference region is set on the reference image, a region corresponding to the reference region is set on the comparison image as a comparison region. Due to the foregoing, a region of concern on the reference image (for example, a portion in which a change is caused by a disease)

can be distinguished from the comparison region to be compared on the comparison image.

In the image displaying apparatus of the sixth embodiment of the present invention, a plurality of images read out from the storage unit are subjected to image processing, so that a new image is generated. The processed image and the images read out are displayed in such a manner so as to be alternately changed over. In this way, it is possible to compare the original image stored in the storage unit with the images that have been subjected to image processing. In the image processing, images are processed so that differences between the reference image in the plurality of images read out from the storage unit and the images can be corrected. Due to the correction, the conditions with respect to the geometry, density and contrast of the radiographic object are made to be the same, so that images can be easily compared with each other.

DETAILED DESCRIPTION OF THE INVENTION

Embodiments of the present invention will be described below.

Figure 1:
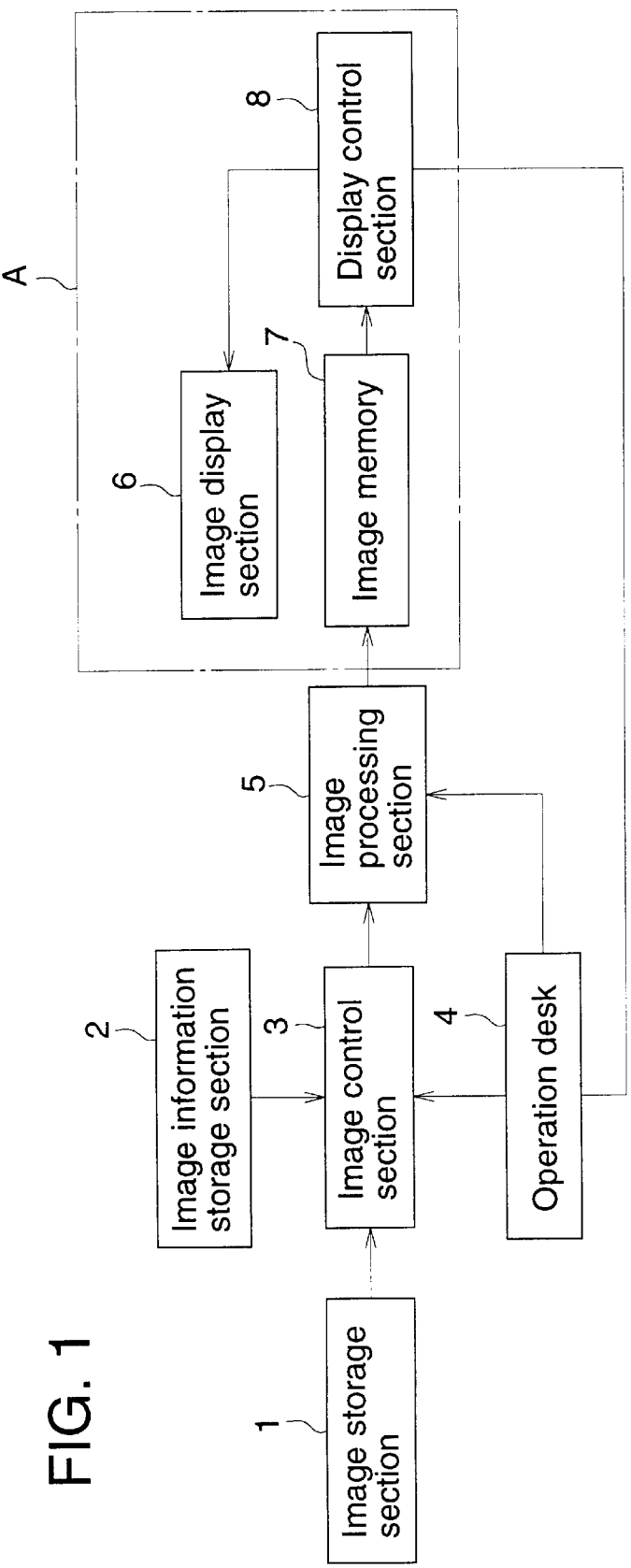
FIG. 1 is a structural diagram of the first and second embodiments of the present invention.

FIG. 1 is a structural diagram of the embodiment of the displaying apparatus of the processed image from temporally sequential images according to the present invention.

In FIG. 1, the image storage section 1 stores a plurality of frames of digital image data of the X ray image that has been taken for medical diagnosis use, for example, a radiographic image of the chest of a human body that has been acquired in a routine medical checkup. Specifically, the image storage section 1 is composed of a magneto-optical disk.

The above radiographic image data will be explained as follows. A silver halide film on which a radiographic image is recorded is exposed to the beams of light emitted from a light source such as a laser or a fluorescent lamp. In this way, transmission light of a silver halide film is provided. This transmission light is subjected to photoelectric conversion, so that the radiographic image data can be provided. Alternatively, after radioactive rays have been transmitted through a radiographic object, they are absorbed by photo-stimulable phosphor. After that, the phosphor is excited by light or thermal energy, and radioactive ray energy stored in the phosphor is emitted in the form of photostimulated luminescence. This photostimulated luminescence is subjected to photoelectric conversion, so that the radiographic image data can be provided.

There is provided an image information storage section 2 separately from the image storage section 1. In this image information storage section 2, various information about each image stored in the image storage section 1 is stored. Examples of the information about each image to be stored are: image acquisition date, study type radiographic exposure condition, image processing condition, patient information, registration information of the images on which the same portion of the same patient has been radiographed, and result of detection of abnormalities.

In this case, the registration information is defined as follows. In a plurality of images including a common radiographic object portion, in order to register the position of the common radiographic object portion between the plurality of images, at least one of the plurality of images is subjected to geometric transformation. The registration information is used for this geometric transformation. Due to the registration information, a positional discrepancy of the radiographic object in the process of photographing and a relative positional discrepancy caused by the difference of X ray projection are corrected by the geometric transformation in accordance with the registration information, so that the same portions on a plurality of images can be accurately superimposed on each other in accordance with the structure.

The image data stored in the image storage section 1 and various auxiliary information stored in the image information storage section 2 are checked by the image control section 3 and read out. In this case, the image information storage section 2 may be omitted, and both image data and various information corresponding to the image data may be stored together in the image storage section 1.

When an image to be read out is arbitrarily selected through the operational desk 4, the data stored in the image storage section 1 and the image information storage section 2 are read out by the image control section 3 (image reading means) at any time. When necessary, the image data that has been read out is subjected to image processing by the image processing section 5 (image processing means). Then the image data is displayed on the image display section 6 of the image display unit A (image display means) so that the image can be inspected.

According to the conventional method, when a radiographic film is inspected on a viewing box, the target film must be sought and set on the viewing box. However, according to the method of the invention, the aforementioned work is not required. Therefore, it is possible to inspect the image effectively.

The image display unit A includes the image display section 6, image memory 7, and display control section 8. CRT, plasma display and liquid crystal display are used for the image display section 6. From the viewpoint of performance to display the contrast, it is preferable to use CRT. It is more preferable to use a high definition CRT for medical use, the number of scanning lines of which is not less than 1000.

The image data read out from the image storage section 1, or the image data subjected to image processing after being read out, is stored in the image memory 7 in the image display unit A. The image data stored in the image memory 7 is controlled by the display control section 8 and displayed in the image display section 6. The display control section 8 controls the display image in accordance with a command of display format given through the operational desk 4.

Concerning the patient who receives a routine medical checkup periodically, X ray photographing is conducted on the chest periodically. Therefore, temporally sequential images are provided for each patient.

In this way, a plurality of temporally sequential images of the same portion of the same patient are photographed at different points of time. When the temporally sequential images thus obtained are subjected to subtraction processing, which is one type of temporally sequential image processing, it is possible to selectively emphasize a portion of the patient which has been temporally changed. Accordingly, when the subtraction image, which is an image generated by the subtraction processing, is observed, a portion that has been temporally changed can be easily detected, that is, a portion that has been changed by a disease can be easily found.

In this case, the subtraction processing is an image processing defined as follows. A difference between the pixel values of corresponding pixels on two images is calculated. The thus obtained difference is given as a pixel value of the processed image. Processing from temporally sequential images is an image processing defined as follows. Image data of temporally sequential images is subjected to computer analysis, so that one processed image is generated. In the case of computer analysis, after the completion of registration processing, the subtraction processing is conducted.

In the second embodiment, the temporally sequential images (original images) are previously subjected to the subtraction processing, and the thus obtained subtraction image (image processed from temporally sequential images) is stored in the storage section 1 together with the temporally sequential images. Alternatively, in the first embodiment, a plurality of temporally sequential images are read out from the storage section 1, and the subtraction image is newly generated in the image processing section 5 (temporally sequential image processing means) in accordance with the plurality of images that have been read out. When the subtraction image obtained by either method is processed and displayed as described later, a portion which has been temporally changed can be easily detected.

Figure 2:
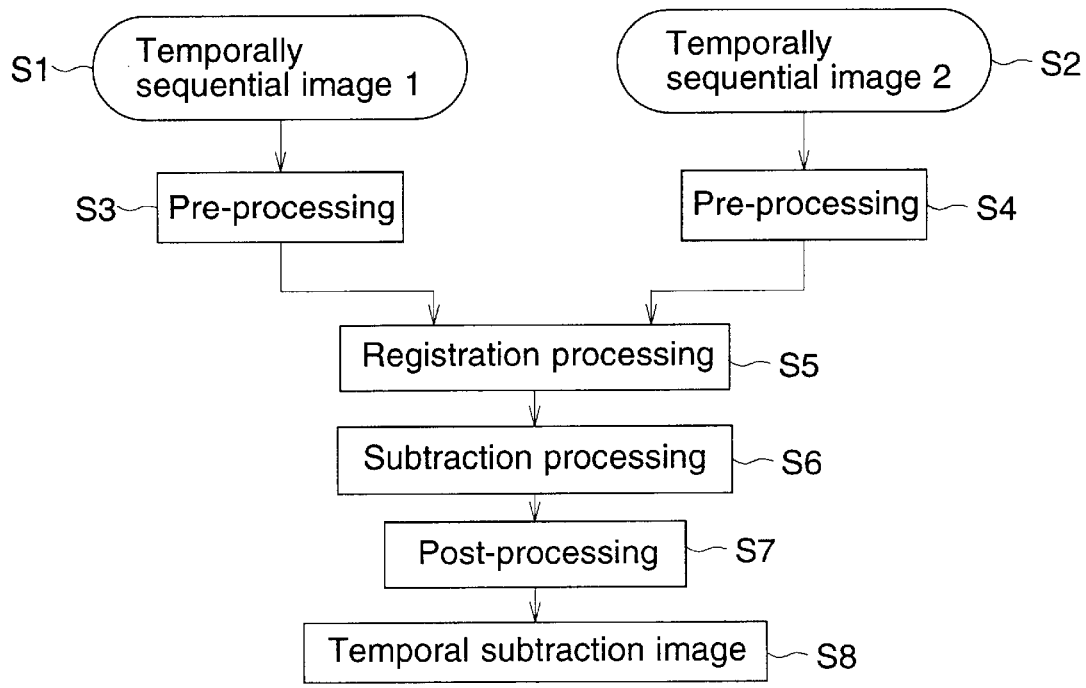
FIG. 2 is a flowchart showing the subtraction processing in the present invention.

For example, the subtraction processing is conducted as shown by the flowchart in FIG. 2. First, the temporally sequential images (1) and (2), which are shown in S1 and S2, are subjected to pre-processing (S3, S4). In this case, the pre-processing is a reduction processing of images for simplifying the computation of subtraction processing. For example, the number of pixels is reduced, and average processing is conducted.

The pre-processing includes a reduction processing. The pre-processing further includes a density correction, contrast conversion, edge enhancement or blurring and magnification processing.

After the completion of pre-processing, registration processing is conducted in order to adjust the relatively positional discrepancy of the radiographic object portion caused by the positioning of the radiographic object in the process of photographing and also caused by the difference of the X ray (S5) projection.

The method of registration processing described above is disclosed Japanese Patent Publication No. 14553/1986 and Japanese Patent Publication Open to Public Inspection Nos. 278183/1988.

Specifically, the registration processing is carried out as follows. For example, a positional discrepancy between the corresponding portions on two images are found by means of linear approximation, and a correction function to correct a nonlinear positional discrepancy between the two images is found using an amount of positional discrepancy found in the above manner. Alternatively, the following composition may be adopted. After registration processing has been roughly conducted in accordance with the parameters input from the outside, an amount of the positional discrepancy is calculated for each corresponding region by the cross-correlation method, so that the deformation can be corrected.

Information of the registration described above is given in the forms of an amount of shift, a combination of the amount of shift and the amount of rotation, number of the order of the polynomials (in the case of polynomial transformation), a combination of the amount of shift in the X-direction and the amount of shift in the Y-direction with respect to all pixels, and a combination of the amount of shift in the X-direction and the amount of shift in the Y-direction with respect to the representative pixel.

In this connection, registration processing may be conducted in accordance with the registration information previously stored. Alternatively, registration processing may be conducted in such a manner that a positional discrepancy between the images which have been read out is detected and the registration information is set in accordance with the result of detection.

After the completion of registration processing, subtraction processing is carried out for effecting a subtraction between pixel values of the corresponding pixels of two temporally sequential images (S6), so that a subtraction image can be obtained. Next, post-processing such as processing for adding a predetermined offset value and processing for adjusting the contrast is conducted (S7). In this way, a subtraction image finally obtained in accordance with the temporally sequential image can be set (S8). This subtraction image is a subtraction image which is a type of the processed image from temporally sequential images.

In this case, the post-processing includes a contrast manipulation (contrast conversion). The post-processing may include edge enhancement or blurring, and a thresholding.

Figure 3:
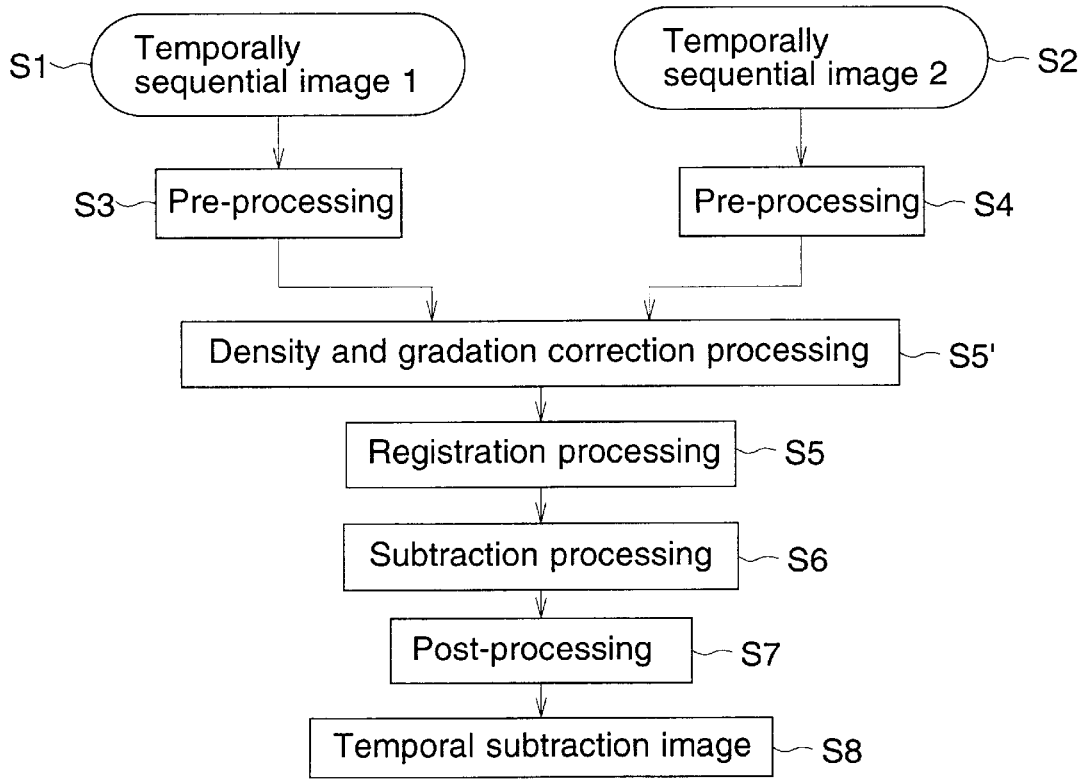
FIG. 3 is a flowchart showing the subtraction processing in the present invention.

In this connection, as illustrated in the flowchart of FIG. 3, immediately before or immediately after the registration processing (S5), density and contrast correction processing (S5') may be conducted, by which the overall density and contrast of an image is adjusted to the standard density and contrast characteristics. Specifically, density and contrast manipulation disclosed in the United States Patent Publication No. 5224177 may be employed. Alternatively, the following method may be adopted. An image is divided into a plurality of small regions, and pixel values of one of the images are corrected so that the statistical values of the pixels in the corresponding small regions are unified, wherein the statistical values include an average and a standard deviation.

In this connection, in the aforementioned subtraction image, which is an image processed from temporally sequential images, the portion which has temporally changed is emphasized so that the changed portion can be easily detected, however, a portion which has not temporally changed is difficult to be found on the image. Accordingly, even when a portion which has temporally changed, that is, even when a portion which has changed due to a disease is detected, it is difficult to accurately locate it in the normal structures from the same subtraction image.

In order to solve the above problems, the following measures are taken in this embodiment. The image addition means conducts processing in such a manner that the temporally sequential image (the original image) is added to the processed image from temporally sequential images. When the thus generated addition image is displayed, the portion which has temporally changed can be clearly distinguished from the portion of the normal structures which has not changed. In this way, the image can be easily read by a person in charge of inspection.

That is, when the temporally sequential image, which is an original image, is added to the subtraction image, it is possible to obtain an image having a portion with an interval change selectively emphasized and a portion with the normal structures which have not temporally changed also displayed. Therefore, the portion which has temporally changed can be distinguished from the normal structures which has not temporally changed. An example of the above addition processing will be explained below.

In this case, the addition processing is an image processing defined as follows. A sum of the pixel values of the corresponding pixels on two images is calculated. The thus obtained value is given as a pixel value of the processed image.

Figure 4:
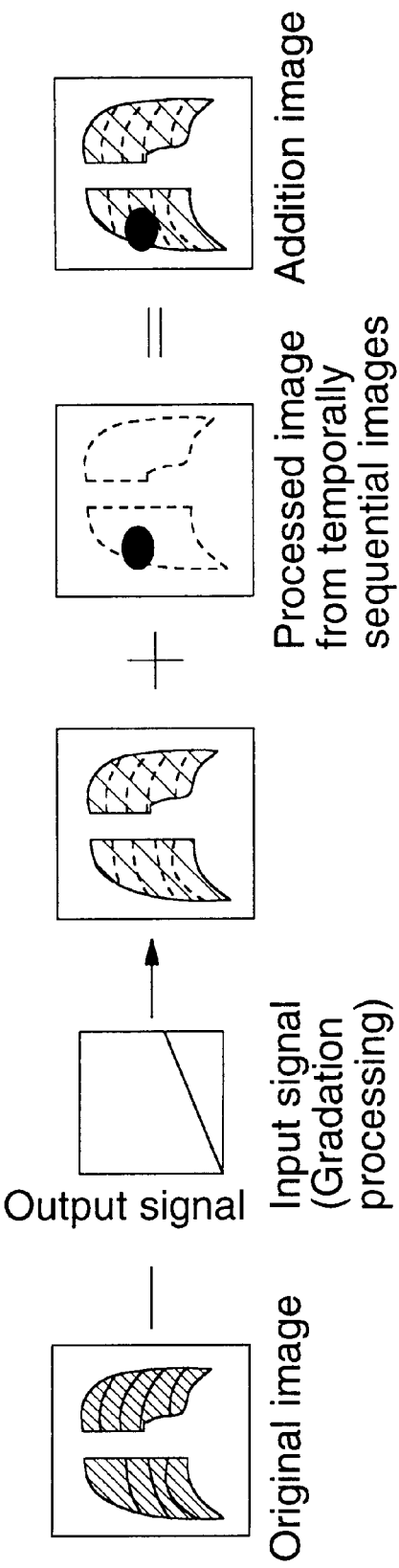
FIG. 4 is a view showing an addition image when the original image is subjected to contrast manipulation.
Figure 5:
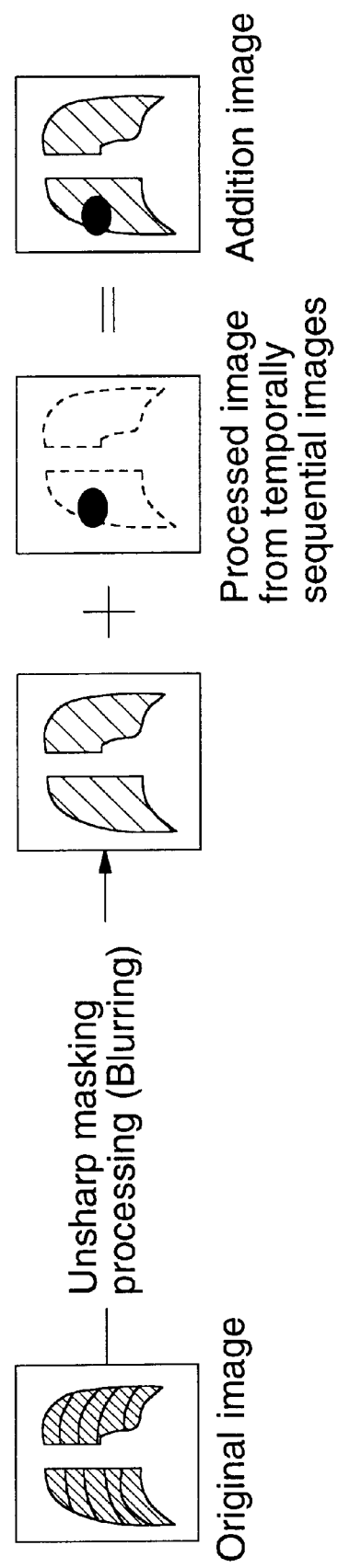
FIG. 5 is a view showing an addition image when the original image is subjected to unsharp masking processing.
Figure 6:
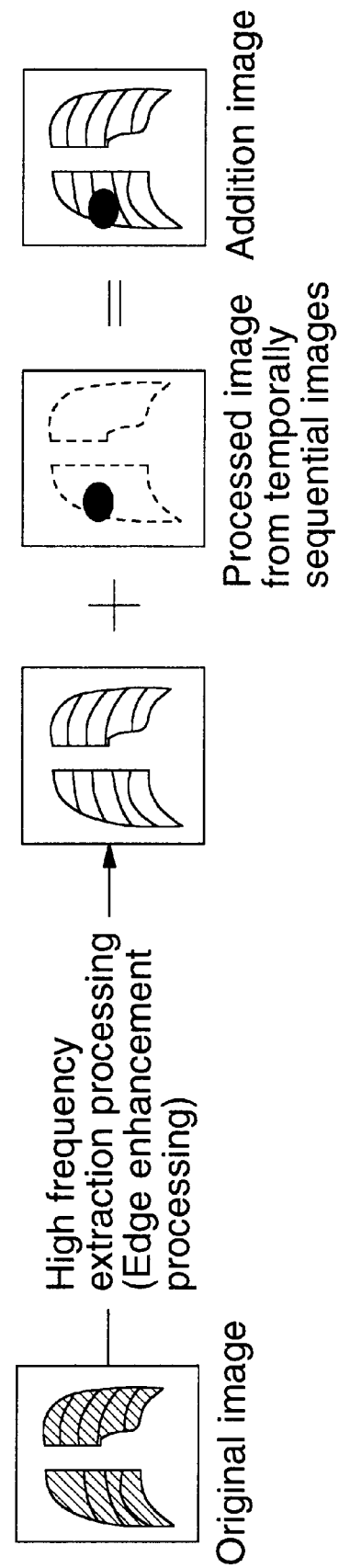
FIG. 6 is a view showing an addition image when the original image is subjected to high frequency extraction processing.

FIGS. 4 to 6 show an example in which the operation is conducted as follows. After image processing has been conducted on the one of temporally sequential images (the original image) by the image processing means, the image is added to the subtraction image by the image addition means, and the addition image is displayed by the image display means.

The example shown in FIG. 4 is operated as follows. After the one of temporally sequential images have been subjected to contrast manipulation using the contrast conversion table by the contrast manipulation means, the one of temporally sequential images subjected to image processing (contrast manipulation) is added to the subtraction image by the image addition means, so that the thus obtained addition image is displayed by the image display means.

When the contrast of the one of temporally sequential images is lowered, the portion which has temporally changed, to be emphasized on the subtraction image, is prevented from the difficulty in which the changed portion becomes difficult to be detected due to camouflaging by the unchanging normal structures on the addition image. Due to the foregoing, while the portion with an interval change emphasized on the subtraction image is easy to be inspected, the portion can be superimposed on the image of the structure which has not temporally changed. When the above addition image is observed, the changed portion can be clearly distinguished from the portion which has not temporally changed, so that the changed portion can be easily detected.

An example shown in FIG. 5 is composed in the following manner. The one of temporally sequential images is subjected to unsharp masking processing which is blurring, by the edge enhancing and blurring means. Then the image is added to the subtraction image by the image addition means. The thus obtained addition image is displayed by the image display means.

The unsharp masking processing described above is defined as follows. An average of image data is found for each of a plurality of image regions composed of a plurality of pixels arranged in the longitudinal and transverse directions. The thus obtained average is replaced with the pixel value of the pixel at the center in the image region. In this way, a blurred image is generated.

When the unsharp masking processing is conducted on the one of temporally sequential images, it is possible to prevent the portion with an interval change, which is emphasized by the subtraction image, from being embedded in the portion without an interval change on the addition image. Therefore, a position and region of the portion with an interval change can be accurately detected.

Further, in the example shown in FIG. 6, high frequency extraction processing is conducted on the one of temporally sequential images by the edge enhancing and blurring means, the edge enhancement of the one of temporally sequential images is conducted. Therefore, it is possible to prevent the portion with an interval change, which is emphasized on the subtraction image, from camouflaged by the structure on the addition image. Due to the foregoing, the portion with an interval change can be easily distinguished.

In the above example, after the one of temporally sequential images (the original image) has been subjected to image processing such as contrast manipulation and blurring by the image processing means, the image is added to the subtraction image (the processed image from temporally sequential images). On the contrary, after the subtraction image has been subjected to image processing, the image may be added to the one of temporally sequential images. An example corresponding to this composition is shown in FIG. 7.

Figure 7:
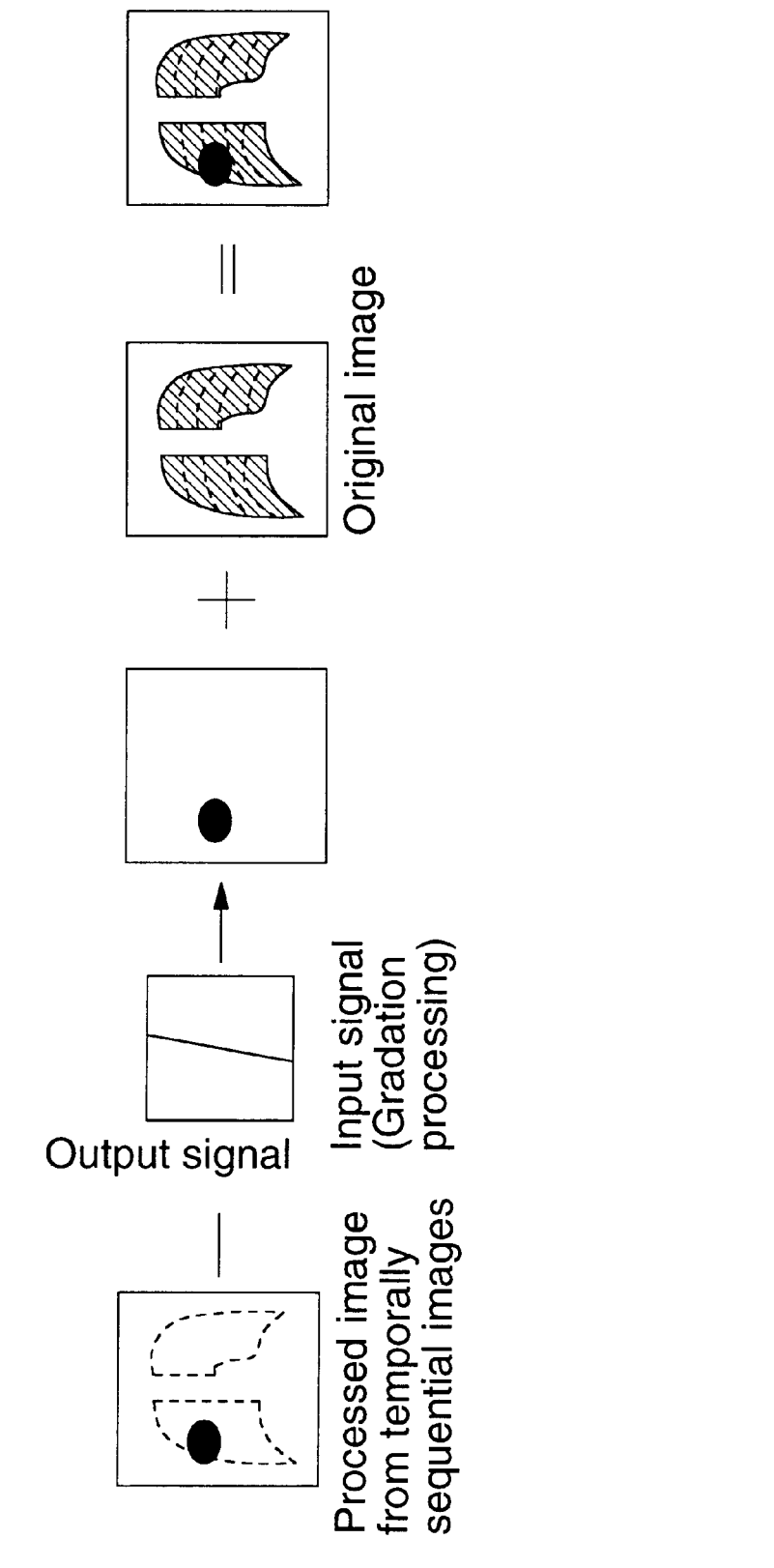
FIG. 7 is a view showing an addition image when the processed image from temporally sequential images is subjected to contrast manipulation.

An example shown in FIG. 7 is composed as follows. The subtraction image (the processed image from temporally sequential images) is subjected to contrast manipulation, by which the contrast is emphasized, by converting image data using a predetermined contrast conversion table. This processing is conducted by the contrast manipulation means. When the subtraction image subjected to contrast manipulation is added to the one of temporally sequential images (the original image) by the image addition means, an addition image is obtained. The thus obtained addition image is displayed by the image display means.

As described above, after the contrast manipulation, by which the contrast of the subtraction image is emphasized, has been conducted, the image is added to the one of temporally sequential images, so that the addition image can be obtained. Due to the foregoing composition, it is possible to prevent the portion with an interval change, which is emphasized on the subtraction image, from being embedded in a shade of the one of temporally sequential images on the addition image. Accordingly, the portion which has temporally changed is clearly distinguished from the normal structures.

Instead of the above contrast manipulation, the following composition may be adopted. Blurring to remove the high frequency components on the subtraction image is conducted. In the case of finding the subtraction image, after the high frequency artifact caused by a small positional discrepancy of the ribs or blood vessels has been removed, the image may be added to the one of temporally sequential images.

Figure 8:
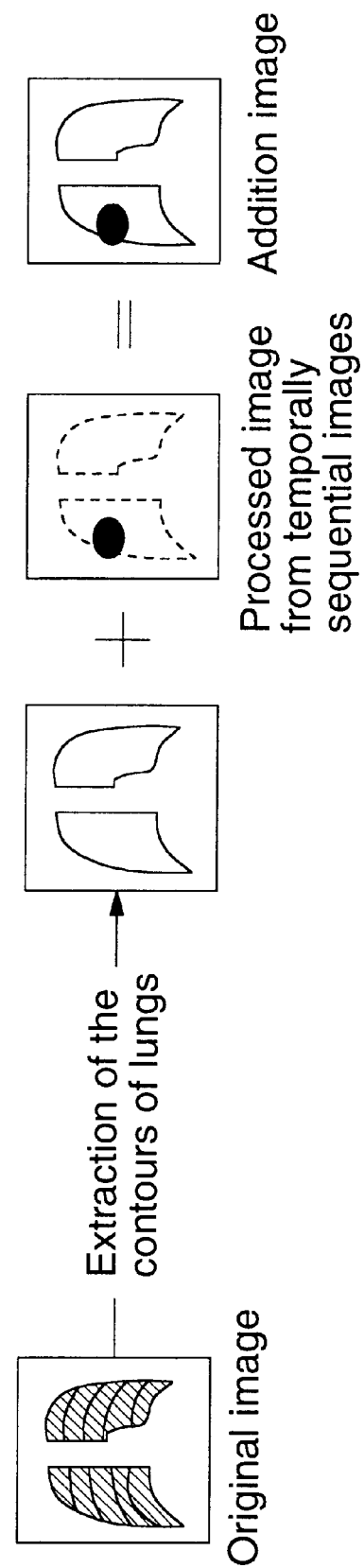
FIG. 8 is a view showing an addition image when the contour of a structure is extracted from the original image.

Further, in the example shown in FIG. 8, after the one of temporally sequential images (the original image) has been subjected to image processing, the image is added to the subtraction image (the processed image from temporally sequential images). In this case, the operation is conducted as follows. The feature extraction means conducts processing by which the contours of the feature such as lung boundaries, rib boundaries and spinal lines are extracted from the one of temporally sequential images. At the same time, the figure generation means generates figures to express the contours with lines. The subtraction image is added to the figure to express the contours by the image addition means. In this way, the image on which the portion with an interval change is emphasized is superimposed on the contours of the structure.

In this case, the feature extraction processing is an image processing defined as follows. A position of the desired feature on the image is specified by means of computer analysis conducted on image data. The desired feature may be an anatomic feature such as lung boundaries. Alternatively, the desired feature may be a set of pixels satisfying a predetermined condition in such a manner that the pixel value exceeds a predetermined threshold value.

It is possible to find the contour extraction described above from the profile information as shown in Japanese Patent O.P.I. Publication No. 240832/1988.

In this connection, instead of expressing the contours by lines, in accordance with the result of extraction of the contours, the lung and heart regions may be painted out on the figure.

When the structure is extracted and formed into a figure as described above, the portion which has temporally changed can be clearly distinguished from the structure.

Figure 9:
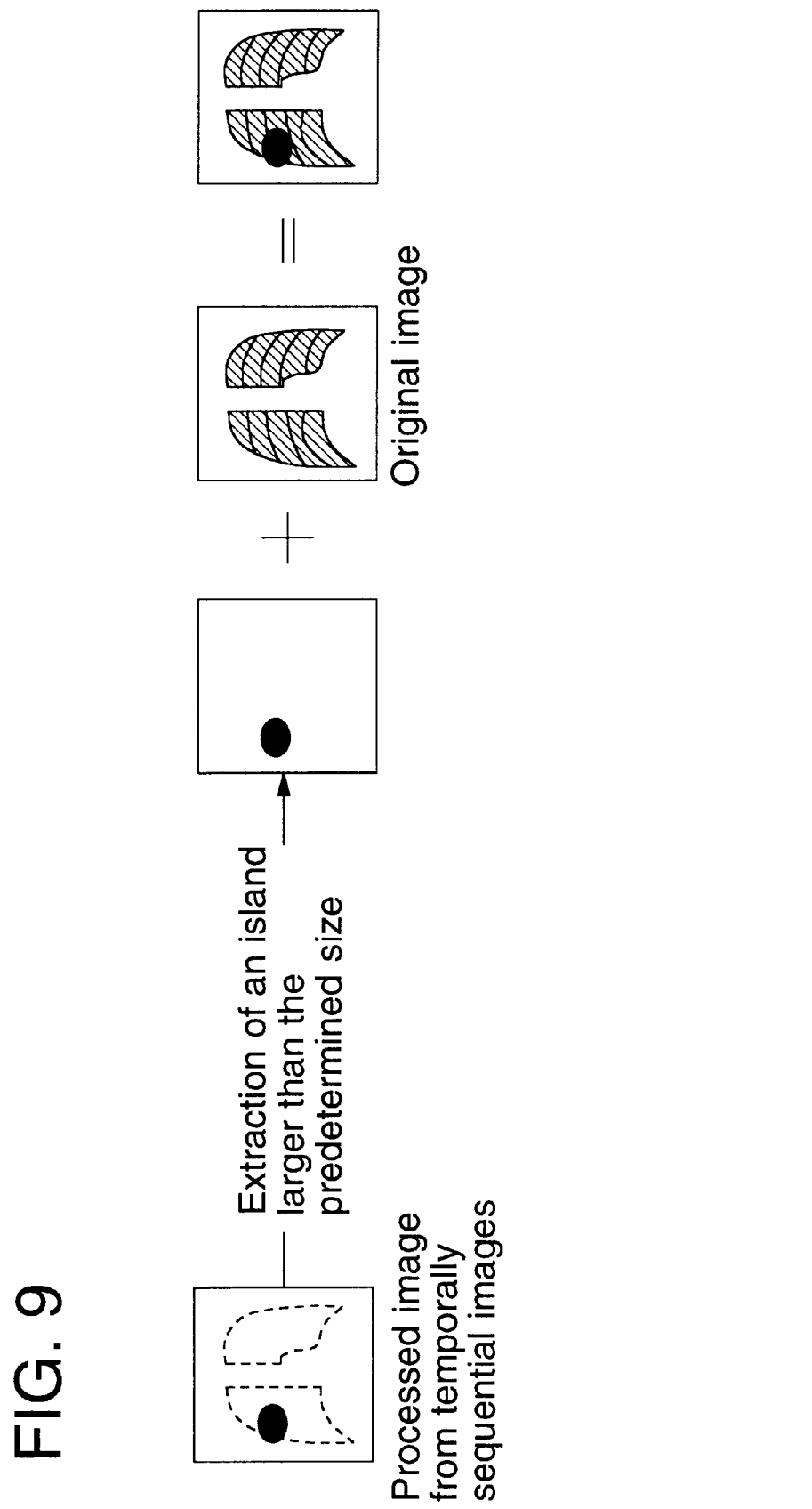
FIG. 9 is a view showing an addition image when a portion with an interval change, the size of which is larger than the predetermined value, is extracted from the processed image from temporally sequential images.
Figure 10:
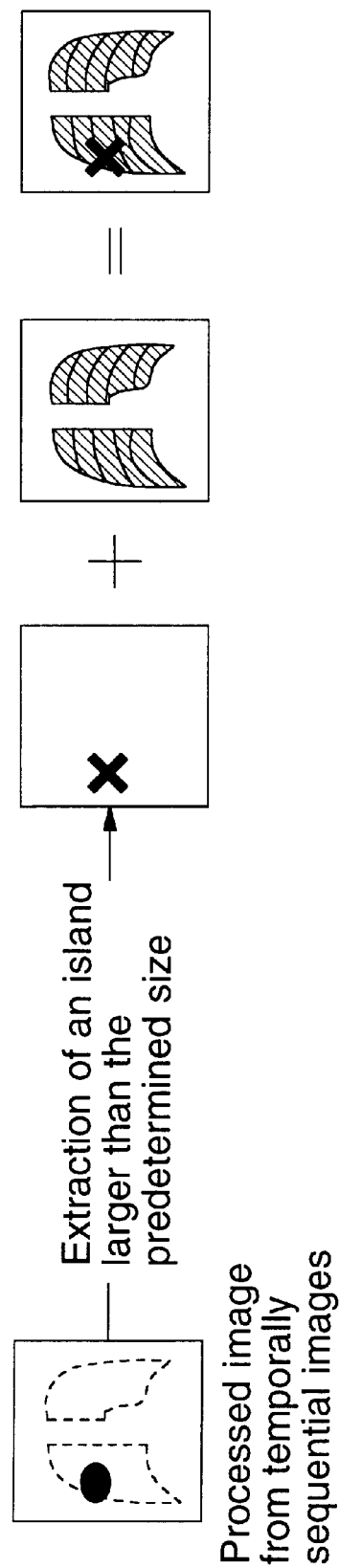
FIG. 10 is a view showing an addition image when a portion with an interval change, the size of which is larger than the predetermined value, is extracted from the processed image from temporally sequential images.

In the example shown in FIG. 9, the subtraction image is binarized in accordance with the comparison of the image data of each pixel of the subtraction image (the processed image from temporally sequential images) with a predetermined threshold value. Due to the thresholding processing described above, an unnecessary image portion caused by a small positional discrepancy of the ribs and blood vessels caused in the case of finding the subtraction image can be removed. Then, a region is found in which a plurality of images not less than the threshold value corresponding to the portion with an interval change, continue. Then, labeling processing for discriminating each region is conducted. In this way, a region (island), the dimensions of which are larger than the predetermined values, is extracted in this region. The thus extracted region is painted out. In this case, the aforementioned image on which the portion with an interval change is painted out is added to the one of temporally sequential images (the original image), and the thus obtained addition image is displayed.

According to the above composition, while an unnecessary image portion caused by the positional discrepancy between the images when the subtraction image is found by the binarization of the subtraction image, is removed, the portion which temporally changed can be emphasized. Accordingly, when the image is added to one of the temporally sequential images, the portion which has temporally changed is not camouflaged by the normal anatomic structures. Accordingly, in this case, the portion which has temporally changed can be clearly distinguished from the normal anatomic structures which has not temporally changed.

The portion which has temporally changed extracted by the binarization of the subtraction image is painted out. Further, the portion may be expressed by an annotation (mark X in the drawing) which is put at the center of the region in which an interval change has been caused.

In the above examples, after the one of the temporally sequential images (the original image) and the subtraction image (the processed image from temporally sequential images) has been subjected to image processing, both are added to each other so that the addition image can be obtained. However, after both the one of the temporally sequential images (the original image) and the subtraction image (the processed image from temporally sequential images) have been subjected to image processing, addition may be conducted.

In this connection, the one of the temporally sequential images (the original image), which is a radiographic image, and the subtraction image (the processed image from temporally sequential images) are monochromatic images, the density of which is determined in accordance with an amount of transmitted radioactive rays. When the monochromatic images are colored by image processing (color operation means), it is possible to express the portion which has temporally changed so that the portion can be easily recognized.

In the above color operation, for example, the one of the temporally sequential images (or the image obtained when the one of the temporally sequential images has been subjected to image processing) and the subtraction image (or the image obtained when the subtraction image has been subjected to image processing) may be expressed by different colors. Due to the above composition, on the addition image, the portion which has temporally changed can be easily distinguished from the normal anatomic structures, and the positional relation between the portion which has temporally changed and the normal anatomic structures can be made clear.

As illustrated in FIG. 8, when the contour of the structure is extracted on the one of temporally sequential images, the lines or the painted pattern may be expressed by a color, and the background of the contour image may be expressed as a monochromatic image.

Further, the following composition may be adopted. The one of temporally sequential images is not be colored, and only the subtraction image (or the image obtained when the subtraction image is subjected to image processing) is colored. After the colored image processed from temporally sequential images has been generated, the addition processing is conducted, and the normal feature is expressed as a monochromatic image and only the portion which has temporally changed is expressed by a color.

Figure 11:
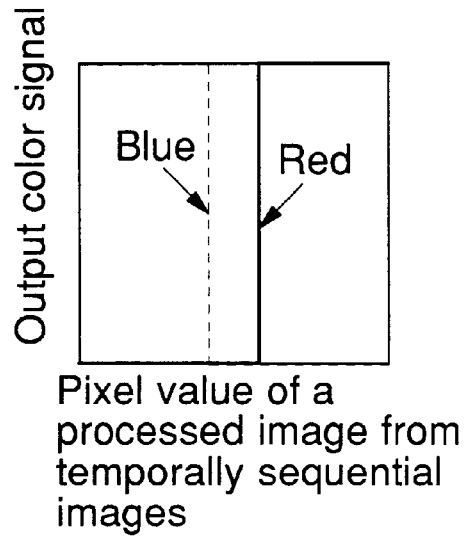
FIG. 11 is a diagram showing the coloring characteristic corresponding to the pixels value of the processed image from temporally sequential images.
Figure 12:
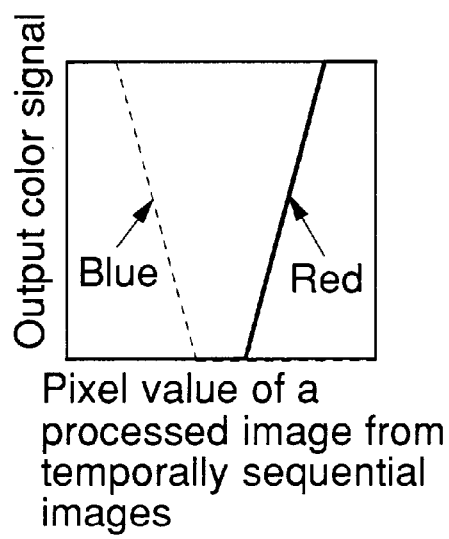
FIG. 12 is a diagram showing the coloring characteristic corresponding to the pixels value of the processed image from temporally sequential images.

As illustrated in FIG. 11, when the subtraction image is colored, the hue may be changed in accordance with the pixel value of the subtraction image (the processed image from temporally sequential images). Further, as illustrated in FIG. 12, the density may be changed together with the hue in accordance with the pixel value.

In the color operation illustrated in FIG. 11, the pixel which has not temporally changed is not colored, and only the pixel which has temporally changed is colored to be red or blue in accordance with the image data changing direction. In the same manner as the color operation shown in FIG. 11, in the color operation shown in FIG. 12, the pixel which has temporally changed is colored by a different color determined in accordance with the direction of the change. Further, the more the change with time advances, the higher the color density is increased.

For example, when the subtraction processing is expressed by the following expression, Subtraction image (Image processed from temporally sequential images)

= (Previous image)−(The latest image)+Constant since the transmission factor of an abnormality caused by a disease is generally low so that the pixel values of that portion are small, by the color operation for the subtraction image illustrated in FIG. 11, a newly generated abnormality is expressed by red since the pixel value of the subtraction image is large, and an improved abnormality is expressed by blue since the pixel value of the subtraction image is small. Accordingly, when the color operation illustrated in FIG. 12 is conducted, the degree of development of an abnormality caused by a disease or the degree of improvement can be estimated by the color density.

As described above, when the addition image generated by various processing is displayed, the portion which has temporally changed can be clearly distinguished from the normal anatomic structures. However, when the portion which has temporally changed is confirmed or observed in detail, in some cases, it becomes necessary to display the subtraction image or the one of temporally sequential images. Consequently, a person who reads images, that is, a doctor may switch the images through the operational desk 4 between the addition image and the one of temporally sequential images, or between the addition image and the subtraction image, or among the addition image, the one of temporally sequential images and the subtraction image (display switching means).

Concerning the switch pattern of the display image, for example, the one of temporally sequential images of the subtraction image is usually displayed. When a request is made through the operational desk 4, the addition image is displayed. Alternatively, the addition image is usually displayed, and when a request is made through the operational desk 4, the one of temporally sequential images or the subtraction image is displayed.

When the displayed image is switched as described above, the portion which has temporally changed can be easily confirmed by the comparison of the addition image with the subtraction image. After the confirmation of the portion which has temporally changed, the portion which has temporally changed can be observed in detail by the one of temporally sequential images.

In this connection, when a plurality of image display sections 6 are provided, it is possible to simultaneously display the one of temporally sequential images or the subtraction image (the image before the addition processing) together with the addition image on different display images. Further, it is also possible to simultaneously display the one of temporally sequential images or the subtraction image together with the addition image on the same display image, wherein the dimensions of the images are reduced (the plural image display means).

Further, the conditions of image processing such as contrast manipulation, edge enhancing and blurring and color operation may be arbitrarily designated by the person who reads the images through the operational desk 4.

Further, a plurality of addition images obtained when the conditions of image processing such as contrast manipulation, edge enhancing and blurring and color operation are changed in the multi-levels (the processing condition adjusting means) are successively switched in accordance with the commands given through the operational desk 4 (the display switch means). Also, a plurality of addition images obtained when the image processing conditions are changed in the multi-level (the processing condition adjusting means) may be automatically successively switched over at regular intervals (the display switch means. In this case, when the image processing conditions are changed in the multi-level, it is possible to observe the images while the grade of emphasis of the portion which has temporally changed or the normal anatomic structures portion is being changed.

Examples of the image processing conditions to be changed in the multi-level are: the contrast transformation curve of contrast manipulation, the size of the filter or the mask for spatial frequency processing and the threshold value of the thresholding.

When the subtraction processing is conducted in accordance with the registration, some radiographic object portions are not common among the images. In the case where these portions which are not common among the images are included in the periphery of the subtraction image, it is preferable that these unnecessary portions are subjected to masking or trimming so that these portions can be removed.

Next, the second through sixth examples having respectively the constitution shown in FIG. 13 will be explained as follows. In the system shown in FIG. 13, there are provided two image display units A and B (image display means) each having image display section 6, and each of the image display units A and B is provided with image memory 7 and display control section 8 in addition to the image display section 6.

Image data read out of the aforementioned image storage section 1 are stored temporarily in image memory 7a of image display unit A, and when image display unit B is also used for displaying images, the constitution makes the image data to be transferred from the image memory 7a to image memory 7b after being controlled by transfer control section 9. Namely, the constitution wherein two display units A and B are provided makes it possible to display simultaneously at least two images which are different each other. The constitution may also be provided with three or more display units.

The transfer control section 9 transfers image data in accordance with a command of a display form conducted through operation desk 4, and the command of the display form mentioned above is sent also to display control section 8a of image display unit A, and then is given also to display control section 8b after being controlled by the transfer control section 9. In the display control section 8, image data to be displayed on image display section 6 are processed so that images are displayed in accordance with a designated display form.

The aforementioned processing of image data includes processes of magnification and size reduction for making images to conform to designated display sizes and contrast manipulation such as window processing for making image contrast to conform to brightness characteristics of a display unit. Incidentally, it is also possible to employ a system wherein the processes of magnification and size reduction and the contrast manipulation mentioned above are carried out in image processing section 5 before images are transferred to an image memory.

Figure 13:
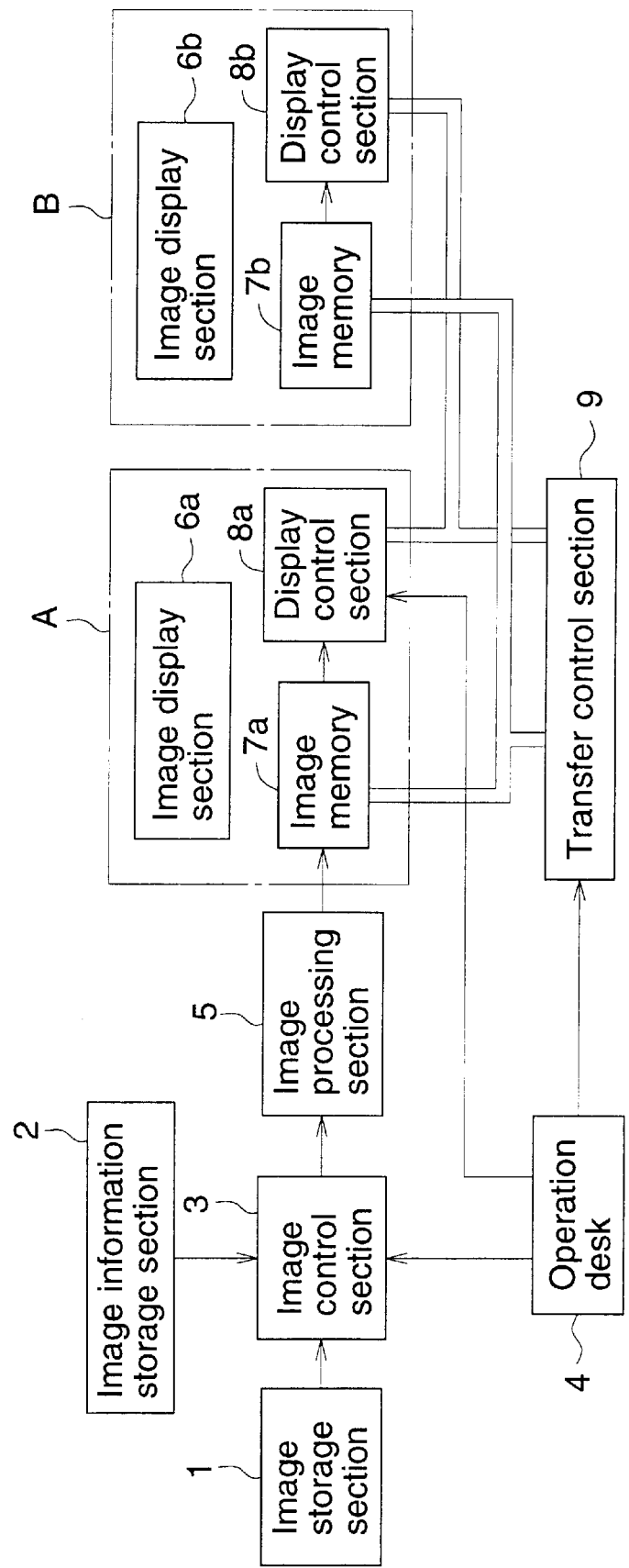
FIG. 13 is a structural diagram of the third to sixth embodiments of the present invention.
Figure 14:
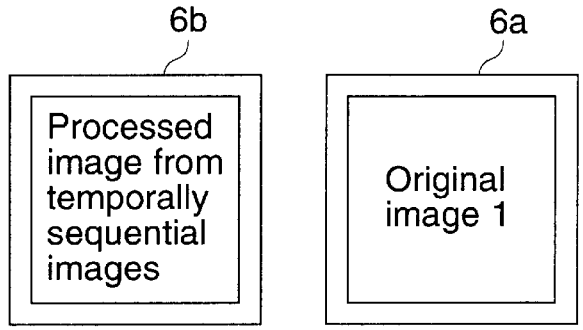
FIG. 14 is a view showing the displaying forms of the original image and the processed image from temporally sequential images.

In the constitution shown in FIG. 13, when either one among a temporal subtraction image and an original image is read out of storage section 1 selectively and only one of the aforesaid two images is displayed on image display section 6, or when only a temporal subtraction image is displayed when the temporal subtraction image is generated in image processing section 5, it is not possible to confirm on the original image quickly the portion with an interval change observed on the temporal subtraction image, resulting in poor diagnostic accuracy and diagnostic efficiency.

In the example, therefore, as the constitution for displaying simultaneously the aforesaid processed image from temporally sequential images (subtraction image from temporally sequential images) and the original image (one of temporally sequential images) on the same display image plane or on different display image planes, a collation between a processed image from temporally sequential images and an original image was made easy so that the portion with an interval change observed on the processed image from temporally sequential images can be confirmed quickly on the original image.

To be concrete, original image (1) (the latest image among temporally sequential images) is displayed on the screen of image display section 6a in image display unit A, while, a processed image from temporally sequential images (temporal subtraction image) is displayed on the screen of image display section 6b in the other image display unit B arranged in parallel with the aforesaid image display section 6a, as shown in FIG. 4, so that the original image and processed image from temporally sequential images can be displayed on different display image planes simultaneously for collation. Owing to this, when the portion with an interval change is observed based on the processed image from temporally sequential images (subtraction image from temporally sequential images), the corresponding portion can be confirmed quickly on the original image that is displayed sideways.

In this case, the processed image from temporally sequential images is displayed for the purpose of detecting the interval change, and existence of change with time and location thereof are read roughly from the processed image from temporally sequential images, and based on the results of that reading, the portion on which an interval change is expected to be caused on the original image can be read in detail for diagnosis.

In the third example, therefore, it is preferable that an original image is displayed without degradation while keeping resolution of image display section 6a for displaying an original image to be equivalent to or higher than the number of pixels of the original image. However, high resolution required for a screen for displaying an original image is not needed because a processed image from temporally sequential images is displayed only for detecting roughly the existence and location of a portion of change with time. Therefore, image display section 6b established in advance to display a processed image from temporally sequential images may have resolution lower than that of image display section 6a and may be smaller in terms of screen size than image display section 6a, though the image display section 6a established in advance as one for displaying an original image is required to have resolution equivalent to or higher than the number of pixels of the original image.

When image display section 6a is of high resolution, it is possible to display images precisely, and a loss of image quality is small even when a plurality of images with size reduction are displayed side by side on the same image plane. Further, it is possible to detect a portion with an interval change without being influenced by shadows of fine normal structures by displaying a processed image from temporally sequential images on a display image plane of relatively low resolution. Furthermore, it is possible to attain cost reduction by requesting image display section 6b to have no resolution which is unnecessarily too high.

To be concrete, it is preferable, from the viewpoint of contrast performance, to use a CRT as image display section 6a, and it is more preferable to use a CRT with scanning lines of not less than 1000 lines which is known as a high definition CRT for medical use. As image display section 6b, it is preferable to use a CRT, a plasma display, a liquid crystal display and others.

As a form of display, it is also possible to employ the constitution wherein an original image and a processed image from temporally sequential images are displayed simultaneously on the same screen on the part of the image display section 6a as shown in FIGS. 15–18.

Figure 15:
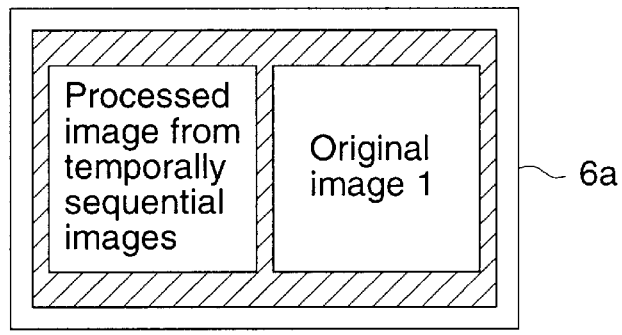
FIG. 15 is a view showing the displaying forms of the original image and the processed image from temporally sequential images.
Figure 16:
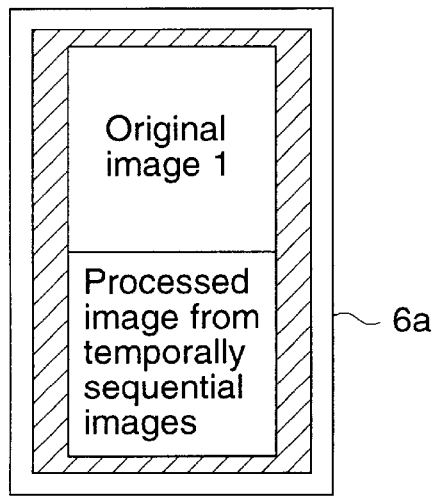
FIG. 16 is a view showing the displaying forms of the original image and the processed image from temporally sequential images.

In the examples shown in FIGS. 15 and 16, an original image and a processed image from temporally sequential images are reduced to the same size and displayed on the same screen. In the example shown in FIG. 15, the original image and the processed image from temporally sequential images are displayed side by side on the same screen of the image display section 6a, while, in the example shown in FIG. 16, the original image is displayed at the upper portion of a portrait screen and the processed image from temporally sequential images is displayed at the lower portion thereof.

Figure 17:
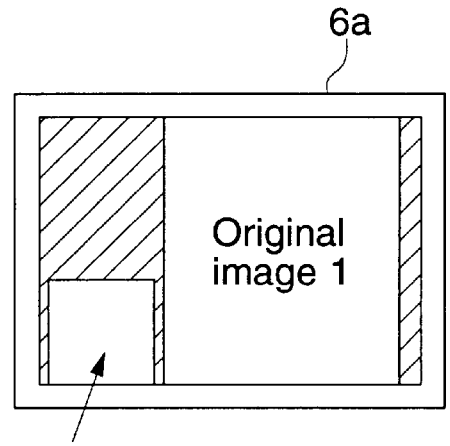
FIG. 17 is a view showing the displaying forms of the original image and the processed image from temporally sequential images.
Figure 18:
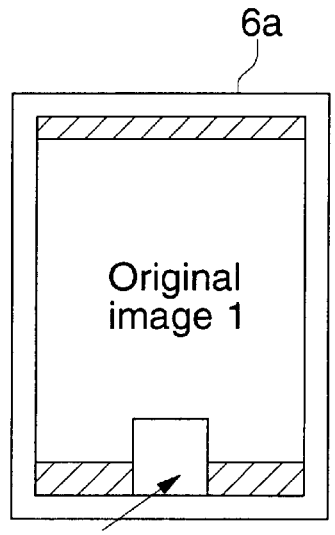
FIG. 18 is a view showing the displaying forms of the original image and the processed image from temporally sequential images.

In the fourth example shown in FIGS. 17 and 18, a reduction factor for a processed image from temporally sequential images is made larger relatively than that for an original image, and both of the original image and the processed image from temporally sequential images are simultaneously displayed side by side on the same screen of image display section 6a. In the example shown in FIG. 17, two images which are different in image size (reduction factor) each other are displayed side by side, while, in the example shown in FIG. 18, the original image is displayed at the upper portion of a portrait screen and the processed image from temporally sequential images with a large reduction factor is displayed below the aforementioned original image in a manner that a part of the processed image from temporally sequential images is overlapped on the original image.

With regard to a temporally sequential image, it is not necessary to read fine structures, and reading of the fine structures sometimes disturbs detection of portion with an interval change. Therefore, display after reduction with a large reduction ratio does not cause any problem, and a large reduction ratio makes fine structures which are not necessary for observation of the portion with an interval change to disappear and thereby makes it easy to detect the portion with an interval change.

Figure 19:
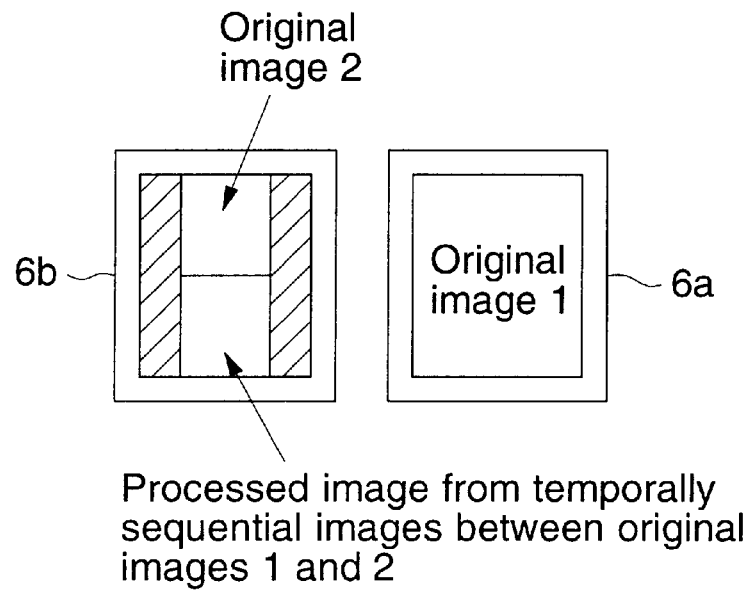
FIG. 19 is a view showing the displaying forms of the original image and the processed image from temporally sequential images.

Further, with regard to a display of an original image (one of temporally sequential images) in the constitution in the example shown in FIG. 19, two original images (1) and (2) which are used in obtaining a processed image from temporally sequential images are displayed simultaneously without limiting to only the latest one (1). Namely, in the example shown in FIG. 19, the latest original image (1) is displayed on image display section 6a without reduction, while, on image display section 6b, original image (2) radiographed previously and a processed image from temporally sequential images (one of temporal subtraction images) generated by the use of two original images (1) and (2) are displayed vertically after being reduced.

Figure 20:
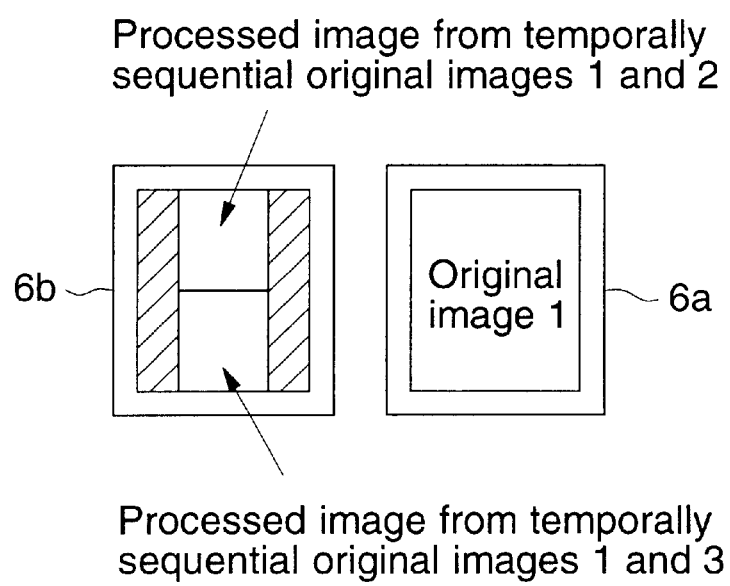
FIG. 20 is a view showing the displaying forms of the original image and the processed image from temporally sequential images.

In the example shown in FIG. 20, the latest original image is displayed on image display section 6a without being reduced in the same manner as in the example shown in FIG. 19, while, on image display section 6b, two processed images from temporally sequential images generated based on a combination of two different temporally sequential images are displayed vertically after being reduced. The upper image of the two processed images from temporally sequential images displayed on the image display section 6b mentioned above is a subtraction image between the latest original image (1) and preceding original image (2), while, the lower one is a subtraction image between the latest original image (1) and the second image previous to the latest original image (3). By displaying these two processed images from temporally sequential images, it is possible to present an interval change of a radiographic object in a period from the preceding radiographing to the latest radiographing as well as that in a period from the second radiographing previous to the latest radiographing to the latest radiographing.

Further, in the example shown in FIG. 20, it is also possible to employ constitution wherein original image (2) and/or original image (3) is displayed on the image display section 6b after being reduced, together with two processed images from temporally sequential images.

Figure 21:
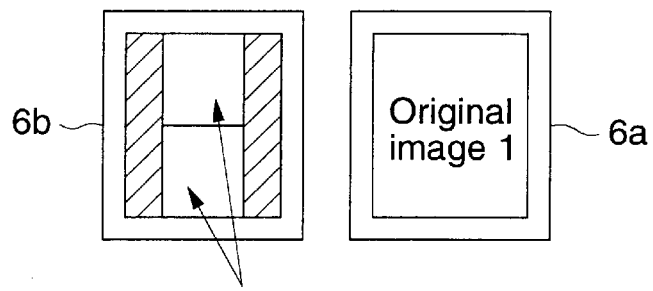
FIG. 21 is a view showing the displaying forms of the original image and the processed image from temporally sequential images.

In the example shown in FIG. 21, on the other hand, original image (1) only is displayed on image display section 6a without being reduced, while, on image display section 6b, two images each being processed under a different processing condition are displayed vertically after being reduced as a processed image from temporally sequential images (temporal subtraction image) generated by subtraction processing between the latest original image (1) and preceding original image (2).

As the aforementioned processing condition, it is possible, for example, to make one to be an ordinary subtraction image and to make the other to be an image obtained from the subtraction image with an inversed gray-scale. Owing to such display, a portion with an interval change is displayed with both black and white, making it easier to detect the portion with an interval change that is based on a processed image from temporally sequential images. It is further possible to employ the constitution wherein two processed images from temporally sequential images obtained by using different standard density and standard contrast in density and contrast correction processing conducted before subtraction processing are displayed simultaneously side by side. Even in this case, detection of a portion with an interval change is easier compared with an occasion to display an individual processed image from temporally sequential images.

Figure 22:
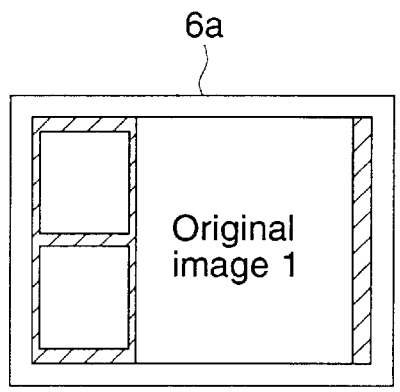
FIG. 22 is a view showing the displaying form in which 3 images including the original image are displayed on 1 image plane.
Figure 23:
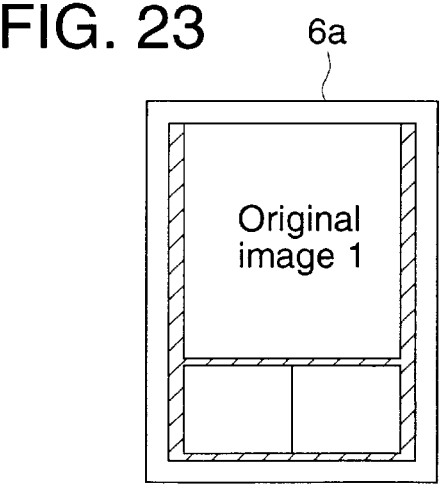
FIG. 23 is a view showing the displaying form in which 3 images including the original image are displayed on 1 image plane.
Figure 24:
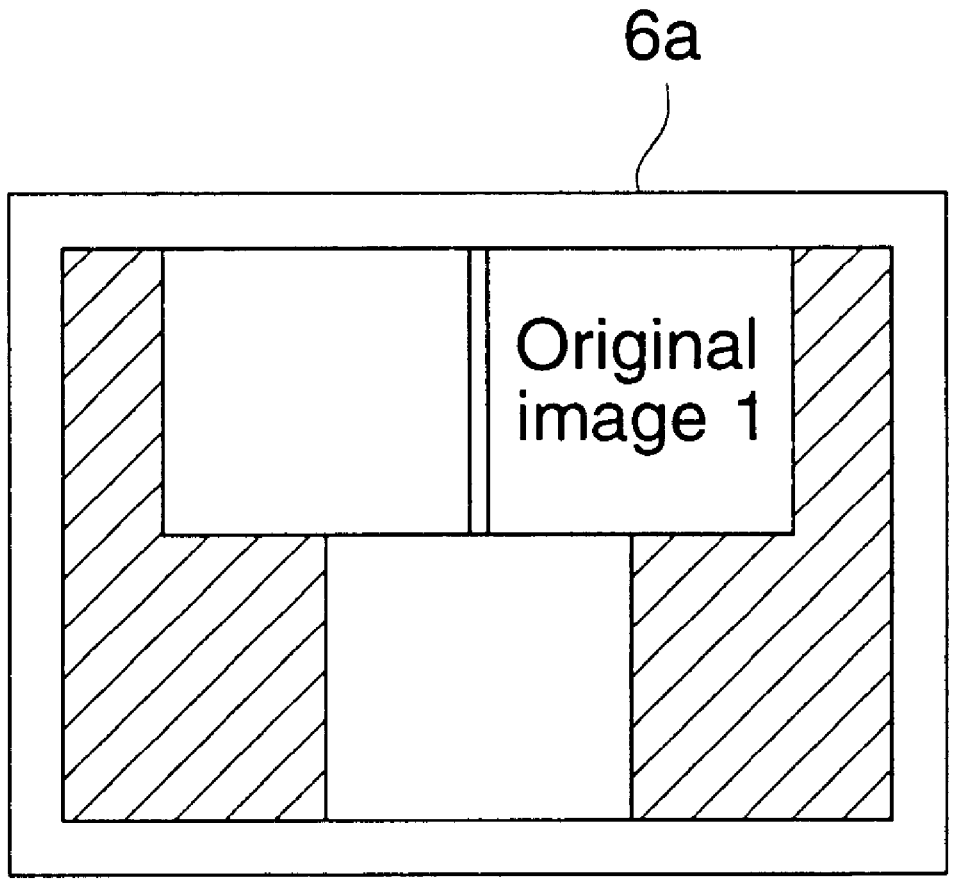
FIG. 24 is a view showing the displaying form in which 3 images including the original image are displayed on 1 image plane.

Incidentally, there may be used either the constitution wherein display as shown in FIGS. 19–21 are conducted using only a screen of image display section 6a as shown in FIGS. 22–24, for example, or the constitution wherein three image display units (image display section 6) are provided, on the contrary, and each of three images shown respectively in FIGS. 19–21 is displayed individually on a screen of the image display section 6.

As shown in FIGS. 15–24, the constitution capable of displaying images after size reduction makes it possible not only to display images at high speed but also to display simultaneously, without using many display image planes, plural images which are based on the latest original image and are useful for diagnosis. In addition, due to display after size reduction, less eye movement is required and observation is easy because images can be positioned closer each other.

As processing to reduce the number of pixels for reduction display, it is possible to use subsampling process or averaged subsampling process. When a reduction ratio is not an integer, interpolation reduction processings such as linear interpolation can be used.

In the example stated above, it is also possible to use the constitution wherein two images selected from plural temporally sequential images, for example, are displayed simultaneously on image display sections 6a and 6b respectively, and the constitution wherein a processed image from temporally sequential images is read or generated selectively based on observation of the two temporally sequential images on the screens, can also be employed.

In the constitution of the example mentioned above, one of temporally sequential images (original image) and a processed image from temporally sequential images (subtraction image from temporally sequential images) are displayed simultaneously either on the same display image plane or on different display image planes for easy collation between images. However, for recognizing accurate position or range of a portion with an interval change or the degree of change thereof by comparing one of temporally sequential images with a processed image from temporally sequential images, it is necessary to select from plural images displayed the small areas corresponding each other based on experience and knowledge and to judge while comparing the small areas with eyes alternately.

In the fifth example shown below, therefore, display is made in a way to make the collation of the portions with an interval change easy so that accuracy and efficiency of diagnosis may be improved.

Figure 25:
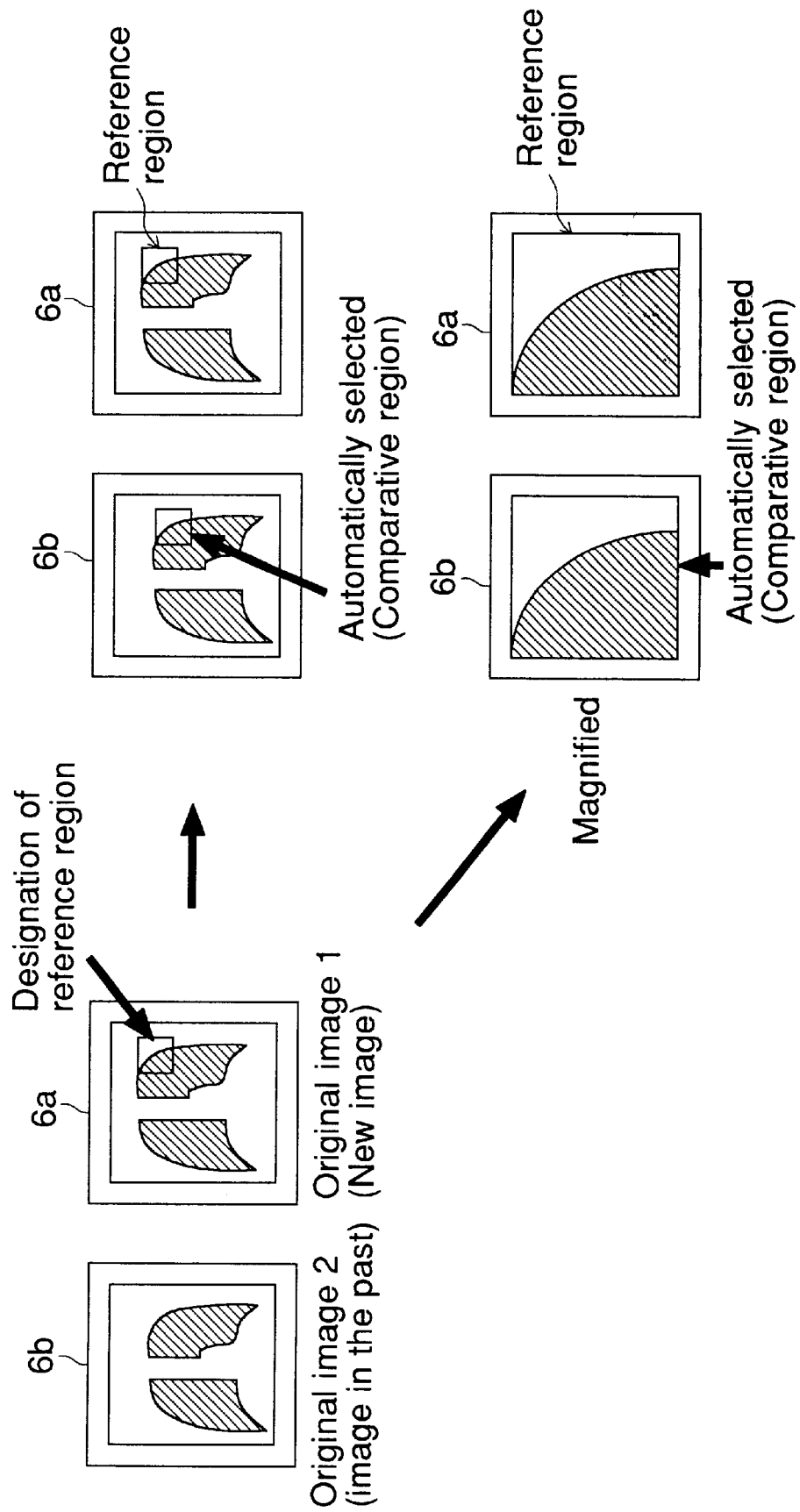
FIG. 25 is a view showing an example in which the reference region on the reference image and the comparison region on the comparison image are illustrated.

Namely, any region in images on the screen can be coordinate-designated through an operation of operation desk 4 (reference region setting means) or the like. For example, when a region concerned on the latest one of temporally sequential images (reference image) is set as a reference region in the case where two temporally sequential images (original images) are displayed simultaneously respectively on image display sections 6a and 6b, a region corresponding to the radiographic object portion identical to the aforesaid set region concerned on a previous image (comparative image) is established automatically as a comparative region (comparative region setting means), and a window-frame-shaped figure showing the aforesaid reference region or comparative region is displayed to be superposed on an image frame on a screen, as shown in FIG. 25.

For the establishing of the reference region mentioned above, a pointing device such as a mouse provided on the operation desk 4 or the like may be used for establishing, or a key board provided on the operation desk 4 may be used for coordinate-inputting. Further, the constitution wherein a touchscreen is provided on each display portion so that any point on the displayed image can be touched for designation, can also be used.

Under the constitution mentioned above, when there is a region concerned whose change with time is required to be recognized, if the region (a reference region) is designated on the reference image, a region to be observed with comparison on the comparative image is enclosed with a window frame to be displayed as a comparative region. Therefore, what has to be observed as a target for comparison is only the image in the window frame in each region, and it is possible to detect efficiently a degree of the change with time for each image, accordingly.

Incidentally, it is also possible to employ the constitution wherein a reference region is established with a previous image as a reference image, and a comparative region to be compared with the aforementioned reference region is established on the latest image. Or, it is further possible to use another constitution wherein a reference region and a comparative region are established in the same manner as in the foregoing, by designating either one of a processed image from temporally sequential images and an original image as a reference image and by designating the other as a comparative image.

Though a reference region may be established freely by means of operation desk 4 as stated above, the constitution stated below may also be used when a processed image from temporally sequential images (subtraction image from temporally sequential images) where a temporal change portion is emphasized and an original image are to be displayed. Namely, in the constitution, a portion of an interval change is detected from the aforesaid processed image from temporally sequential images, and a region including the portion detected is established automatically as a reference region (reference region setting means), and a comparative region corresponding to the reference region mentioned above is established on an original image (comparative region setting means), then, a figure with which the reference region and comparative region can be discriminated is superimposed on both the processed image from temporally sequential images and the original image to be displayed.

It is further possible to employ the constitution wherein a region detected in the past as an abnormality through automated detection or diagnosis by a doctor is stored, and based on the stored data, initial setting of a reference region is carried out.

Under such constitution, a target region can be established on the latest original image based on the results of automated detection of a temporal change portion, and such region can be displayed clearly through display of superimposed figures. Therefore, confirmation of the change with time is more simple.

When a reference region and a comparative region are established in this case, comparison between images is carried out only on the image in the aforementioned region. It is therefore preferable to only display (magnified image display means) the predetermined region magnified on a screen which displays at least one of the reference region and comparative region. (See FIG. 25) When the target region is magnified and displayed as stated above, the change with time can be observed in detail.

It is further preferable to employ the constitution wherein a figure showing a reference region or an image of magnified and displayed reference region can be scrolled on a screen vertically and horizontally (scroll display means) through operation of operation desk 4, and a figure showing a comparative region or an image of magnified and displayed comparative region can be scrolled in synchronization with scroll of the reference region, corresponding to an amount and direction of scroll of the reference region (scroll control means).

In this case, a region where an interval change has been observed, or not only a region concerned but also peripheral areas can easily be observed in detail. Further, comparative observation of the peripheral areas can be conducted easily because a comparative region is also scrolled in synchronization with scrolling of the reference image.

Incidentally, a radiographic object position on the reference image and that on a comparative image are deviated each other when establishing on the comparative image, the same radiographic object portion can not be set as a comparative region even if the coordinate position of the reference region is used as that of a comparative region as it is. Therefore, it is necessary to plan so that the same portion as a radiographic object portion included in the reference region can be established as a comparative region by the use of both the coordinate position of the reference region and image data of the common radiographic object portion.

To be concrete, simple registration can be conducted by detecting a position of a primary structure in a common radiographic object on the reference image and the comparative image, and by using the relative coordinate value established under the consideration that a representative one point in the primary structure is the origin of the coordinate axes. For example, in a chest image, when x coordinates of spinal line and y coordinates of a top of lungs are determined regarding respectively a reference image and a comparative image by the use of a technology disclosed in Japanese Patent O.P.I. Publication No. 77353/1987, and when there are used relative x coordinates and y coordinates whose origins are those mentioned above, mostly the same radiographic object portion can be selected as far as the structure in the lung is concerned even when the relative coordinate position of a reference region is used as that of a comparative region as it is.

In a method of higher accuracy, highly detailed image registration is conducted as in the case of obtaining a subtraction image.

Information for registration for establishing the aforesaid comparative region is given in the various forms including an amount of shift, a combination of the amount of shift and an amount of rotation, number of the order of polynominals (in the case of polynominal transformation), a combination of an amount of shift in the x direction and that in the y direction for all the pixels, and a combination of an amount of shift in the x direction and that in the y direction for the representative pixel.

When a reference region has been established, in this case, information of registration for a partial image in the vicinity of the reference region is generated by the use of image data of a radiographic object portion common to the reference image and the comparative image, and based on such information of registration and coordinates of the reference region, coordinates of a comparative region can be established (coordinate determining means).

Further, it is also possible to use the constitution wherein registration information calculated in advance is stored in image information storage section 2 (storage means) so that the registration information may correspond to image data, and at least a part of the registration information (information in the vicinity of a region designated as a reference region) is read out to be used.

It is further possible to use the constitution wherein registration information is calculated, independently of an image display, by the use of image data of a radiographic object portion common to the reference image and the comparative image (registration information calculating means), and that information is stored in image information storage section 2 so that at least a part of that information is read out to be used when necessary.

With regard to establishment of coordinates of a comparative region based on registration information and coordinates of a reference region (coordinates determining means), coordinates of a center point of the comparative region is determined based on the coordinates of the reference region and the aforementioned registration information, for example, and a region identical to the reference region in size is selected with the determined point for the establishment of coordinates of the comparative region.

It is also possible to determine coordinates of the vertexes of a polygon enclosing a comparative region based on coordinates of the vertexes of a polygon (a rectangle in the example shown in FIG. 25) surrounding the reference region.

It is further possible to store the comparative image whose coordinates have been transformed based on registration information in advance, and to make a region having the same coordinate position as a reference region to be a comparative region.

In the constitution of the example mentioned above, one of temporally sequential images and a processed image from temporally sequential images are displayed simultaneously on the same screen or on the different screens so that comparison reading for these images makes it easy to detect the changes with time, and thereby both efficiency and accuracy of diagnosis may be improved. However, there are some cases wherein the same radiographic object has 3 or more images to be compared, for example, and displaying each of these plural images at the same position on the same screen individually through switching is a convenience to image readings.

In the sixth example, therefore, a mode wherein each of plural images of the same radiographic object is displayed at the same position on the same screen individually through switching is provided for plural images of the same radiographic object, in addition to a simultaneous display mode as that described above.

In the aforementioned mode for displaying images individually through switching, when plural temporally sequential images as in the foregoing or a combination of the temporally sequential images and processed images from temporally sequential images are to be read, each of these plural images is displayed at the same position of image display section 6a by turns.

An interval of the aforementioned switching may be a constant period of time set in advance. However, it is preferable that the interval can be changed freely. It is further preferable that the interval of switching can be instructed by a doctor through operation desk 4 each time in the constitution, and further, a temporary stop for switching images can be conducted freely even in the case of switching at constant intervals.

With regard to an order of images to be displayed, though it may be designated freely, it is also possible to employ the constitution wherein an order of display is determined automatically in accordance with a radiographing sequence based on information of date and time of radiographing stored corresponding to each image. If images are displayed in the order of radiographing through switching, sequential changes of a radiographic object can be grasped properly.

When a plurality of images including temporally sequential images and processed images from temporally sequential images are displayed through switching as in the foregoing, for example, it is further possible to employ the constitution wherein an image that is a standard among the aforementioned plural images (for example, the latest one of temporally sequential images or processed image from temporally sequential images) is displayed in each interval for displaying other plural images through switching. Namely, in that constitution, a reference image is displayed every other occasion of display, and the reference image is displayed without fail immediately before and immediately after the image other than the reference image so that each image other than the reference image can be compared easily with the reference image.

For switching of images, the following constitution may be employed without taking the constitution to switch all images at a time; the constitution wherein a portion where the change with time is large is detected from a processed image from temporally sequential images (subtraction image from temporally sequential images), for example, and switching is started from the portion of the change with time to expand the switching area in all directions, or the constitution wherein switching is started from a portion designated with a pointing device by a doctor as an abnormality or a portion designated as an abnormality in the past, for example, and switching area is expanded gradually in all directions from the aforesaid portion. When plural images are displayed through switching by starting the switching of the images from the region concerned in the constitution as in the foregoing, it is easy to grasp the changes between images in the region concerned.

The aforesaid processed image from temporally sequential images may be that stored in storage section 1 in advance, but it may also be that generated newly by the use of one of temporally sequential images stored as stated above in the constitution (image processing means).

In the display of plural images through switching, when there is dispersion in density and in contrast characteristics, or when there is a positional shear of a radiographic object between images caused by a difference of positioning of a radiographic object in radiographing or of X-ray projections, or when each image is individually magnified, reduced or rotated in image processing and a shape of a radiographic object is different, it is not possible to compare plural images with the eye simultaneously. There is a high possibility that accuracy of reading the aimed radiographic object is influenced by a difference between images which are not related to the radiographic object and is degraded.

Therefore, when images are displayed individually at the same position on the same screen through switching, it is preferable to employ the constitution wherein display of images through switching is conducted after taking the process to correct the difference between images having no relation to the aforesaid radiographic object. To be concrete, an image having least difference from other images among the latest radiographed images or plural images, is specified as a reference image in plural images of the same radiographic object, and other image data are subjected to correction processing (contrast, density correction, image registration correction, magnification and size reduction correction) so that they conform to the reference image.

Incidentally, the images subjected to the correction processing can be stored in storage section 1 again, or the conditions of the correction processing can be stored in image information storage section 2 corresponding to images.

In the invention, a plurality of images of the same radiographic object to be displayed simultaneously or displayed through switching can include plural images obtained by radiographing the same radiographic object simultaneously under different X-ray energy, and energy subtraction images generated through subtraction between the aforementioned images, in addition to the temporally sequential images obtained by radiographing the same radiographic object at different hours or processed images from temporally sequential images generated by the use of the temporally sequential images. As an energy subtraction, it is possible to use processing disclosed in Japanese Patent O.P.I. Publication No. 222034/1985.

As explained above, in the display apparatus for the processed image from temporally sequential images related to the first example, it is possible to show, for easy observation, the relative positional relation and sizes of a portion with an interval change for normal anatomic structures by superimposing the processed image from temporally sequential images wherein a portion with an interval change is selectively emphasized on an original image representing normal structures. For radiographs for medical use, in particular, diagnostic accuracy and diagnostic efficiency can be improved, which is an effect.

In the display apparatus for the processed image from temporally sequential images related to the second example, processed images from temporally sequential images are generated from plural temporally sequential images, and these processed images from temporally sequential images are superimposed on an original image. Therefore, an image capable of showing, for easy observation, the relative positional relation and sizes of a portion with an interval change for normal structures can be obtained based on the one of temporally sequential images, which is an effect.

In the image display apparatus related to the third example, an original image (the latest image among temporally sequential images) that serves as a standard for medical diagnosis, for example, is displayed on a screen having higher resolution, while a processed image from temporally sequential images that serves as a reference for diagnosis is displayed on a screen having lower resolution, thereby it is possible to attain cost reduction by keeping the resolution of a display means to the necessary and lowest level, while assuring diagnostic performance based on reading of the original image.

The image display apparatus related to the fourth example has an effect that it is possible to display plural images simultaneously on the same screen by displaying at least one image among images to be displayed through size reduction. It is another effect that it is possible to use a screen effectively by differentiating the reduction factors for plural images to be displayed simultaneously and by displaying the reference image to be relatively large for assuring reading capability, for example, while displaying an image for just a comparison (for example, a processed image from temporally sequential images or one of temporally sequential images) to be relatively small.

In the image display apparatus related to the fifth example, when a reference region is established on the reference image in plural images to be displayed simultaneously including the reference image and comparison image, a region on the comparison image corresponding to the reference region is established as a comparison region, and thereby it is possible to present so that portions different between images can be compared easily, which is an effect. In particular, a portion with an interval change can be compared easily between one of temporally sequential images and a processed image from temporally sequential images, or between an original image and a processed image from temporally sequential images.

In the image display apparatus related to the sixth example, image processing is carried out to generate new images by using plural images read out from a storage unit, and the images thus generated are displayed through switching alternately together with the images read out. Therefore, it is possible to compare the original images stored in the storage unit with images which are subjected to image processing by the use of the aforesaid original images, which is an effect.

Further, processing for correcting differences from a reference image among plural images read out from the storage unit, is conducted for other images. Therefore, it is possible to display plural images through switching after making their shape, density and contrast indifferent to the change of a radiographic object to be the same conditions, and thereby it is possible to grasp the change of the radiographic object easily, which is an effect.

What is claimed is:

1. An image displaying apparatus comprising:
    a memory for storing a plurality of medical images including temporally sequential images of a common portion of a same patient taken at different points of time;
    an image reader for reading out said plurality of medical images from said memory;
    an image processor for processing at least two of said plurality of medical images read out from said memory according to registration information of said at least two of said plurality of medical images so as to obtain a subtraction image;
    an image adder for adding one of said plurality of medical images read out from said memory to said subtraction image so as to obtain an addition image; and
    a display for simultaneously displaying said addition image and at least one of said plurality of medical images added to said subtraction image, on one of a same screen and respective different screens.

2. The apparatus of claim 1, wherein said image processor includes:
    a processing condition adjusting means for successively switching an image processing condition in multi-levels so as to generate multi-level subtraction images; and
    wherein said multi-level subtraction images are displayed by said display, and said display includes a display switch for successively switching among said multi-level subtraction images displayed by said display.

3. An image displaying apparatus comprising:

a memory for storing a plurality of medical images including temporally sequential images of a common portion of a same patient taken at different points of time;

an image reader for reading out said plurality of medical images from said memory;

an image processor for processing at least two of said plurality of medical images read out from said memory according to registration information of said at least two of said plurality of medical images so as to obtain a subtraction image;

an image adder for adding one of said plurality of medical images read out from said memory to said subtraction image so as to obtain an addition image; and a display for displaying said addition image and at least one of said plurality of medical images added to said subtraction image, said display including a display switch for successively switching among said addition image and at least one of said plurality of images added to said subtraction image.

4. The apparatus of claim 3, wherein said image processor includes:

a processing condition adjusting means for successively switching an image processing condition in multi-levels so as to generate multi-level subtraction images; and wherein said multi-level subtraction images are displayed by said display, and said display switch switches successively among said multi-level subtraction images displayed by said display.

5. An image displaying apparatus comprising:

a memory for storing a plurality of medical images obtained at different points of time including at least an image of a patient and a subtraction image which is processed from temporally sequential images of said patient in accordance with registration information of said plurality of medical images;

an image reader for reading out at least one of said plurality of medical images of said patient and said subtraction image from said memory;

an image adder for adding said one of said plurality of medical images of said patient read by said image reader and said subtraction image so as to obtain an addition image; and a display for simultaneously displaying said addition image and at least one of said plurality of medical images added to said subtraction image, on one of a same screen and respective different screens.

6. The apparatus of claim 5, wherein said processing includes:

a processing condition adjusting means for successively switching an image processing condition in multi-levels so as to generate multi-level subtraction images; and wherein said multi-level subtraction images are displayed by said display, and said display includes a display switch for successively switching among said multi-levels subtraction images displayed by said display.

7. An image displaying apparatus comprising:

a memory for storing a plurality of medical images obtained at different points of time including at least an image of a patient and a subtraction image which is processed from temporally sequential images of said patient in accordance with registration information of said plurality of medical images;

an image reader for reading out at least one of said plurality of medical images of said patient and said subtraction image from said memory;

an image adder for adding said one of said plurality of medical images of said patient read by said image reader and said subtraction image so as to obtain an addition image; and a display for displaying said addition image and at least one of (i) said one of said plurality of medical images added to said subtraction image and (ii) said subtraction image, said display including a display switch for successively switching among said addition image and at least one of said plurality of medical images added to said subtraction image.

8. The apparatus of claim 7, wherein said image processor includes:

a processing condition adjusting means for successively switching an image processing condition in multi-levels so as to generate multi-level subtraction images; and wherein said multi-level subtraction images are displayed by said display, and said display switch switches successively among said multi-level subtraction images displayed by said display.

* * * * *